United States Patent
Gafner et al.

(10) Patent No.: US 11,751,848 B2
(45) Date of Patent: Sep. 12, 2023

(54) METHODS AND APPARATUSES FOR ULTRASOUND DATA COLLECTION

(71) Applicant: BFLY Operations, Inc., Guilford, CT (US)

(72) Inventors: Tomer Gafner, Great Neck, NY (US); Matthew de Jonge, Brooklyn, NY (US); Yang Liu, Hoboken, NJ (US); Igor Lovchinsky, New York, NY (US); Nathan Silberman, Brooklyn, NY (US)

(73) Assignee: BFLY OPERATIONS, INC., Burlington, MA (US)

( * ) Notice: Subject to any disclaimer, the term of this patent is extended or adjusted under 35 U.S.C. 154(b) by 685 days.

(21) Appl. No.: 16/734,888

(22) Filed: Jan. 6, 2020

(65) Prior Publication Data

US 2020/0214674 A1 Jul. 9, 2020

Related U.S. Application Data

(60) Provisional application No. 62/933,297, filed on Nov. 8, 2019, provisional application No. 62/789,467, filed on Jan. 7, 2019.

(51) Int. Cl.
*A61B 8/14* (2006.01)
*A61B 8/00* (2006.01)

(52) U.S. Cl.
CPC .............. *A61B 8/465* (2013.01); *A61B 8/14* (2013.01); *A61B 8/4254* (2013.01); *A61B 2562/0219* (2013.01); *A61B 2562/0223* (2013.01)

(58) Field of Classification Search
CPC .... A61B 2562/0219; A61B 2562/0223; A61B 8/14; A61B 8/4245; A61B 8/4254; A61B 8/4461; A61B 8/461; A61B 8/465; A61B 8/467; A61B 8/5207; A61B 8/5238; A61B 8/5246; A61B 8/54; A61B 8/585
See application file for complete search history.

(56) References Cited

U.S. PATENT DOCUMENTS

| | | |
|---|---|---|
| 9,521,991 B2 | 12/2016 | Rothberg et al. |
| 9,592,030 B2 | 3/2017 | Rothberg et al. |
| 10,628,932 B2 | 4/2020 | Rothberg et al. |
| 10,702,242 B2 | 7/2020 | de Jonge et al. |

(Continued)

FOREIGN PATENT DOCUMENTS

| | | |
|---|---|---|
| WO | WO 2017/182417 A1 | 10/2017 |
| WO | WO 2017/222964 | 12/2017 |
| WO | WO 2017/222970 | 12/2017 |

OTHER PUBLICATIONS

Extended European Search Report dated Jul. 28, 2022 in connection with European Application No. 20738343.1.

(Continued)

*Primary Examiner* — Mark D Remaly
(74) *Attorney, Agent, or Firm* — Osha Bergman Watanabe & Burton LLP

(57) ABSTRACT

Aspects of the technology described herein relate to determining, by a processing device in operative communication with an ultrasound device, a position and/or orientation of the ultrasound device relative to the processing device, and displaying on a display screen of the processing device, based on the position and/or orientation of the ultrasound device relative to the processing device, an instruction for moving the ultrasound device.

16 Claims, 8 Drawing Sheets

(56) References Cited

U.S. PATENT DOCUMENTS

| | | |
|---|---|---|
| 10,706,520 B2 | 7/2020 | Rothberg et al. |
| 2011/0055447 A1 | 3/2011 | Costa |
| 2013/0237811 A1 | 9/2013 | Mihailescu et al. |
| 2015/0173715 A1 | 6/2015 | Raghavan et al. |
| 2015/0265254 A1 | 9/2015 | Ishikawa et al. |
| 2017/0105701 A1 | 4/2017 | Pelissier et al. |
| 2017/0360397 A1 | 12/2017 | Rothberg et al. |
| 2017/0360401 A1 | 12/2017 | Rothberg et al. |
| 2017/0360402 A1 | 12/2017 | de Jonge et al. |
| 2017/0360403 A1 | 12/2017 | Rothberg et al. |
| 2017/0360404 A1 | 12/2017 | Gafner et al. |
| 2017/0360411 A1 | 12/2017 | Rothberg et al. |
| 2017/0360412 A1 | 12/2017 | Rothberg et al. |
| 2018/0225993 A1 | 8/2018 | Buras et al. |
| 2018/0336803 A1* | 11/2018 | Patil ................. A61B 8/523 |
| 2019/0130554 A1 | 5/2019 | Rothberg et al. |
| 2019/0142388 A1 | 5/2019 | Gonyeau et al. |
| 2019/0196600 A1 | 6/2019 | Rothberg et al. |
| 2019/0261957 A1 | 8/2019 | Zaslavsky et al. |
| 2019/0266716 A1 | 8/2019 | Rothberg et al. |
| 2019/0282208 A1 | 9/2019 | Silberman et al. |
| 2019/0307428 A1 | 10/2019 | Silberman et al. |
| 2020/0037986 A1 | 2/2020 | Silberman et al. |
| 2020/0037987 A1 | 2/2020 | Silberman et al. |
| 2020/0037998 A1 | 2/2020 | Gafner et al. |
| 2020/0046322 A1 | 2/2020 | Silberman |
| 2020/0054307 A1 | 2/2020 | Silberman et al. |
| 2020/0060658 A1 | 2/2020 | Gafner et al. |
| 2020/0211174 A1 | 7/2020 | Rothberg et al. |
| 2020/0214672 A1 | 7/2020 | de Jonge et al. |
| 2020/0214674 A1 | 7/2020 | Gafner et al. |
| 2020/0214679 A1 | 7/2020 | Silberman et al. |

OTHER PUBLICATIONS

International Preliminary Report on Patentability dated Jul. 22, 2021 in connection with International Application No. PCT/US2020/012335.

International Search Report and Written Opinion dated Apr. 1, 2020 in connection with International Application No. PCT/US2020/012335.

PCT/US2020/012335, Jul. 22, 2021, International Preliminary Report on Patentability.

PCT/US2020/012335, Apr. 1, 2020, International Search Report and Written Opinion.

* cited by examiner

METHODS AND APPARATUSES FOR ULTRASOUND DATA COLLECTION

CROSS-REFERENCE TO RELATED APPLICATIONS

The present application claims the benefit under 35 U.S.C. § 119(e) of U.S. Patent Application Ser. No. 62/789,467, filed Jan. 7, 2019, and entitled "METHODS AND APPARATUSES FOR ULTRASOUND DATA COLLECTION," which is hereby incorporated herein by reference in its entirety.

The present application claims the benefit under 35 U.S.C. § 119(e) of U.S. Patent Application Ser. No. 62/933,297, filed Nov. 8, 2019, and entitled "METHODS AND APPARATUSES FOR ULTRASOUND DATA COLLECTION," which is hereby incorporated herein by reference in its entirety.

FIELD

Generally, the aspects of the technology described herein relate to ultrasound data collection. Some aspects relate to instructing a user to collect ultrasound data by moving an ultrasound device relative to a subject.

BACKGROUND

Ultrasound devices may be used to perform diagnostic imaging and/or treatment, using sound waves with frequencies that are higher with respect to those audible to humans. Ultrasound imaging may be used to see internal soft tissue body structures, for example to find a source of disease or to exclude any pathology. When pulses of ultrasound are transmitted into tissue (e.g., by using an ultrasound device), sound waves are reflected off the tissue, with different tissues reflecting varying degrees of sound. These reflected sound waves may then be recorded and displayed as an ultrasound image to the operator. The strength (amplitude) of the sound signal and the time it takes for the wave to travel through the body provide information used to produce the ultrasound image. Many different types of images can be formed using ultrasound devices, including real-time images. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the present application, a method of operating an ultrasound system is provided, comprising: determining, by a processing device in operative communication with an ultrasound device, a position and/or orientation of the ultrasound device relative to the processing device; and displaying on a display screen of the processing device, based on the position and/or orientation of the ultrasound device relative to the processing device, an instruction for moving the ultrasound device.

According to an aspect of the present application, an apparatus is provided, comprising a processing device in operative communication with an ultrasound device. The processing device is configured to: determine a position and/or orientation of the ultrasound device relative to the processing device; and display on a display screen of the processing device, based on the position and/or orientation of the ultrasound device relative to the processing device, an instruction for moving the ultrasound device.

Some aspects include at least one non-transitory computer-readable storage medium storing processor-executable instructions that, when executed by at least one processor, cause the at least one processor to perform the above aspects and embodiments. Some aspects include an apparatus having a processing device configured to perform the above aspects and embodiments.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
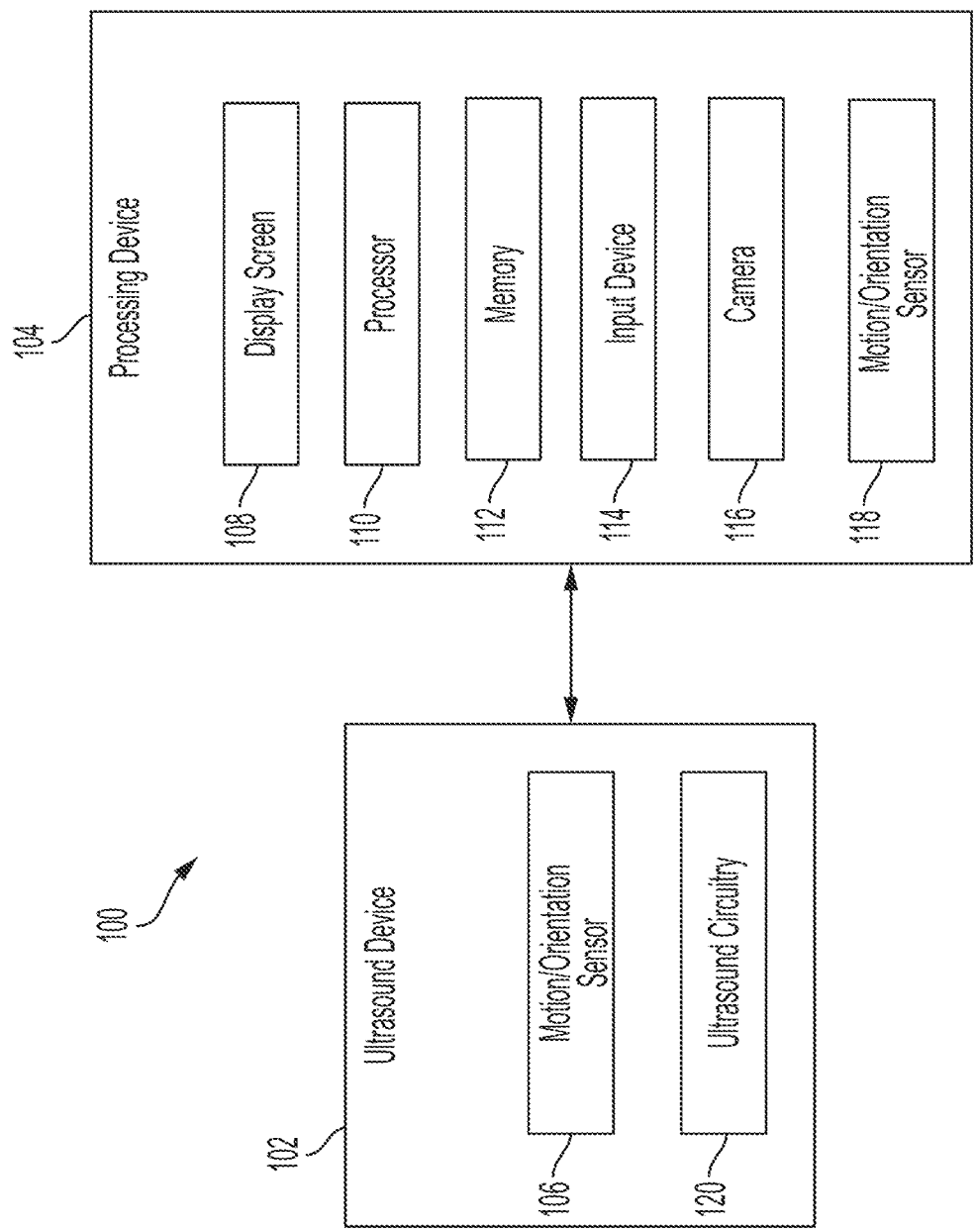
FIG. 1 illustrates a schematic block diagram of an example ultrasound system upon which various aspects of the technology described herein may be practiced.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), and published as U.S. Pat. Pub. No. 2017/0360397 A1, which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of ultrasound imaging devices may make them more accessible to the general populace, people who could make use of such devices may have little to no training for how to use them. Ultrasound examinations often include the acquisition of ultrasound images that contain a view of a particular anatomical structure (e.g., an organ) of a subject. Acquisition of these ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may make the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include capturing ultrasound images of the incorrect anatomical structure and capturing foreshortened (or truncated) ultrasound images of the correct anatomical structure.

Accordingly, assistive ultrasound imaging technology based on artificial intelligence has been developed for instructing an operator of an ultrasound device how to move the ultrasound device relative to an anatomical area of a subject in order to capture a medically relevant ultrasound image. The operator, for example, may be a medical professional at a small clinic without a trained ultrasound technician on staff. The clinic may purchase an ultrasound device to help diagnose patients. In this example, the medical professional at the small clinic may be familiar with ultrasound technology and human physiology, but may know neither which anatomical views of a patient need to be imaged in order to identify medically-relevant information about the patient nor how to obtain such anatomical views using the ultrasound device. The assistive ultrasound imaging technology may provide instructions to the medical professional to correctly position the ultrasound device in order to capture a medically relevant ultrasound image. In some implementations of this technology, an augmented reality (AR) interface includes a video of the ultrasound device and the subject's body, as well as a directional indicator (e.g., an arrow) superimposed on the video that indicates a direction relative to the subject that the operator should move the ultrasound device in order to collect the ultrasound image. Further description of generating instructions for moving the ultrasound device may be found in U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1, which is incorporated by reference herein in its entirety.

The inventors have recognized that it may be helpful for an instruction such as an arrow to be displayed in an AR interface such that the arrow appears relative to the location and orientation of the ultrasound device. For example, the position and orientation of the arrow may be based on the position and orientation of the ultrasound device relative to the processing device. This may help the instruction to be more compelling and useful. Accordingly, the inventors have developed technology for determining, based on video captured by a processing device that depicts an ultrasound device and based on motion and/or orientation data from the processing device and ultrasound device, a position and orientation of the ultrasound device relative to the processing device It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates a schematic block diagram of an example ultrasound system 100 upon which various aspects of the technology described herein may be practiced. The ultrasound system 100 includes an ultrasound device 102 and a processing device 104.

The ultrasound device 102 includes a sensor 106 and ultrasound circuitry 120. The processing device 104 includes a camera 116, a display screen 108, a processor 110, a memory 112, an input device 114, and a sensor 118. The processing device 104 is in wired (e.g., through a lightning connector or a mini-USB connector) and/or wireless communication (e.g., using BLUETOOTH, ZIGBEE, and/or WiFi wireless protocols) with the ultrasound device 102.

The ultrasound device 102 may be configured to generate ultrasound data that may be employed to generate an ultrasound image. The ultrasound device 102 may be constructed in any of a variety of ways. In some embodiments, the ultrasound device 102 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data. The ultrasound circuitry 120 may be configured to generate the ultrasound data. The ultrasound circuitry 120 may include one or more ultrasonic transducers monolithically integrated onto a single semiconductor die. The ultrasonic transducers may include, for example, one or more capacitive micromachined ultrasonic transducers (CMUTs), one or more CMOS (complementary metal-oxide-semiconductor) ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 120 (e.g., transmit circuitry, receive circuitry, control circuitry, power management circuitry, and processing circuitry) to form a monolithic ultrasound device. The ultrasound device 102 may transmit ultrasound data and/or ultrasound images to the processing device 104 over a wired (e.g., through a lightning connector or a mini-USB connector) and/or wireless (e.g., using BLUETOOTH, ZIGBEE, and/or WiFi wireless protocols) communication link.

The sensor 106 may be configured to generate data regarding acceleration of the ultrasound device 102, data regarding angular velocity of the ultrasound device 102, and/or data regarding magnetic force acting on the ultrasound device 102 due to the local magnetic field, which in many cases is simply the field of the earth. The sensor 106 may include an accelerometer, a gyroscope, and/or a magnetometer. Depending on the sensors present in the sensor 106, the data generated by the sensor 106 may describe three degrees of freedom, six degrees of freedom, or nine degrees of freedom for the ultrasound device 102. For example, the sensor 106 may include an accelerometer, a gyroscope, and/or magnetometer. Each of these types of sensors may describe three degrees of freedom. If the sensor 106 includes one of these sensors, the sensor 106 may describe three degrees of freedom. If the sensor 106 includes two of these sensors, the sensor 106 may describe two degrees of freedom. If the sensor 106 includes three of these sensors, the sensor 106 may describe nine degrees of freedom. The ultrasound device 102 may transmit data to the processing device 104 over a wired (e.g., through a lightning connector or a mini-USB connector) and/or wireless (e.g., using BLUETOOTH, ZIGBEE, and/or WiFi wireless protocols) communication link.

Referring now to the processing device 104, the processor 110 may include specially-programmed and/or special-purpose hardware such as an application-specific integrated circuit (ASIC). For example, the processor 110 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network. The processing device 104 may be configured to process the ultrasound data received from the ultrasound device 102 to generate ultrasound images for display on the display screen 108. The processing may be performed by, for example, the processor 110. The processor 110 may also be adapted to control the acquisition of ultrasound data with the ultrasound device 102. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

The processing device 104 may be configured to perform certain of the processes described herein using the processor 110 (e.g., one or more computer hardware processors) and one or more articles of manufacture that include non-transitory computer-readable storage media such as the memory 112. The processor 110 may control writing data to and reading data from the memory 112 in any suitable manner. To perform certain of the processes described herein, the processor 110 may execute one or more processor-executable instructions stored in one or more non-transitory computer-readable storage media (e.g., the memory 112), which may serve as non-transitory computer-readable storage media storing processor-executable instructions for execution by the processor 110. The camera 116 may be configured to detect light (e.g., visible light) to form an image or a video. The display screen 108 may be configured to display images and/or videos, and may be, for example, a liquid crystal display (LCD), a plasma display, and/or an organic light emitting diode (OLED) display on the processing device 104. The input device 114 may include one or more devices capable of receiving input from a user and transmitting the input to the processor 110. For example, the input device 114 may include a keyboard, a mouse, a microphone, touch-enabled sensors on the display screen 108, and/or a microphone. The sensor 118 may be configured to generate motion and/or orientation data regarding the processing device 104. Further description of the sensor 118 may be found with reference to the sensor 106. The display screen 108, the input device 114, the camera 116, the speaker 106, and the sensor 118 may be communicatively coupled to the processor 110 and/or under the control of the processor 110.

It should be appreciated that the processing device 104 may be implemented in any of a variety of ways. For example, the processing device 104 may be implemented as a handheld device such as a mobile smartphone or a tablet. Thereby, a user of the ultrasound device 102 may be able to operate the ultrasound device 102 with one hand and hold the processing device 104 with another hand. In other examples, the processing device 104 may be implemented as a portable device that is not a handheld device, such as a laptop. In yet other examples, the processing device 104 may be implemented as a stationary device such as a desktop computer. For further description of ultrasound devices and systems, see U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application).

FIG. 1 should be understood to be non-limiting. For example, the ultrasound device 102 and/or the processing device 104 may include fewer or more components than shown.

Figure 2:
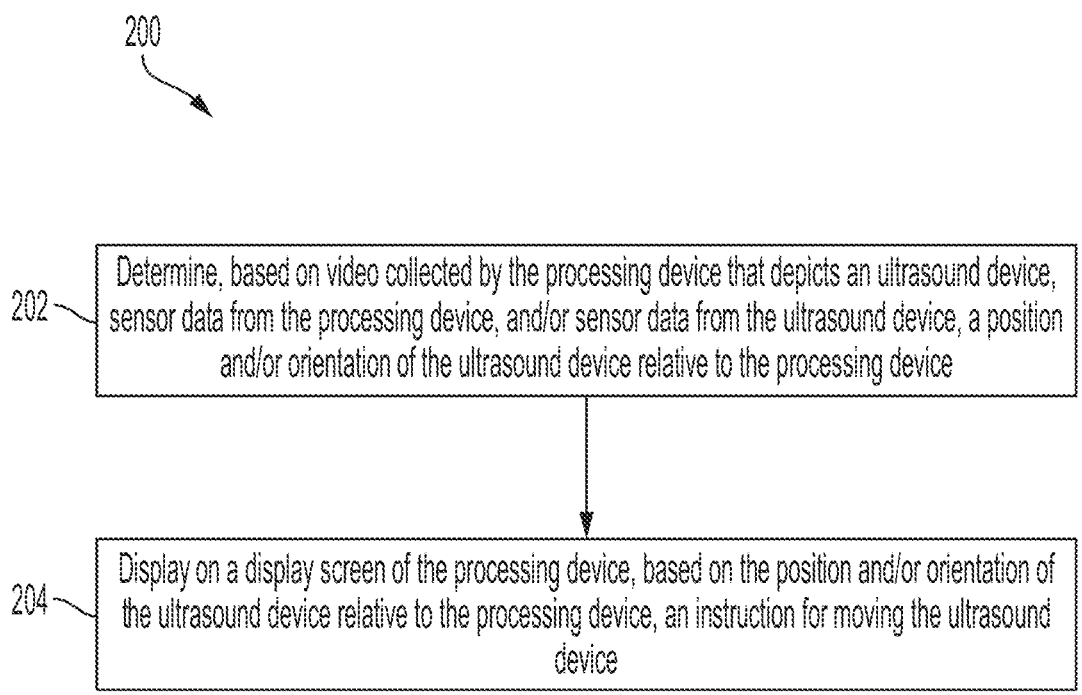
FIG. 2 illustrates an example process for instructing a user to collect ultrasound data, in accordance with certain embodiments described herein.
Figure 3:
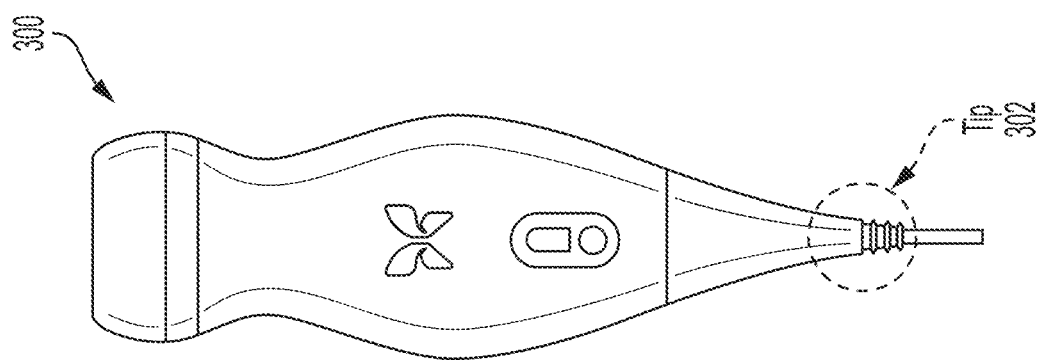
FIG. 3 illustrates an example of the tip of an ultrasound device, in accordance with certain embodiments described herein.

FIG. 2 illustrates an example process 200 for instructing a user to collect ultrasound data, in accordance with certain embodiments described herein. The process 200 is performed by a processing device (e.g., the processing device 104).

In act 202, the processing device determines, based on video collected by the processing device that depicts an ultrasound device (e.g., the ultrasound device 102), sensor data from the processing device, and/or sensor data from the ultrasound device, a position and/or orientation of the ultrasound device relative to the processing device. In some embodiments, the processing device may be in operative communication with an ultrasound device.

The video may be collected by a camera on the processing device (e.g., the camera 116). In some embodiments, a user may hold the ultrasound device in one hand and hold the processing device in the other hand such that the ultrasound device is in view of the camera on the processing device. In some embodiments, a user may hold the ultrasound device in one hand and a holder (e.g., a stand having a clamp for holding the processing device) may hold the processing device such that the ultrasound device is in view of the camera on the processing device.

The position of the ultrasound device relative to the processing device may include components along three degrees of freedom, namely the position of the ultrasound device along the horizontal, vertical, and depth dimensions relative to the processing device. In some embodiments, determining the horizontal and vertical components of the position of the ultrasound device relative to the processing device may constitute determining, for a given frame of video, the horizontal and vertical coordinates of a pixel in the video frame that corresponds to the position of a particular portion of the ultrasound device in the video frame. In some embodiments, the particular portion of the ultrasound device may be the tip of the ultrasound device. FIG.

3 illustrates an example of the tip 302 of an ultrasound device 300, in accordance with certain embodiments described herein.

Referring still to FIG. 2, in some embodiments, the processing device may use a statistical model trained to determine the horizontal and vertical components of the position of the ultrasound device relative to the processing device. In some embodiments, the statistical model may be trained as a keypoint localization model with training input and output data. Multiple images of the ultrasound device may be inputted to the statistical model as training input data. As training output data, an array of values that is the same size as the inputted image may be inputted to the statistical model, where the pixel corresponding to the location of the tip of the ultrasound device (namely, the end of the ultrasound device opposite the sensor portion) in the image is manually set to a value of 1 and every other pixel has a value of 0. (While values of 1 and 0 are described, other values may be used instead.) Based on this training data, the statistical model may learn to output, based on an inputted image (e.g., a frame of the video of the ultrasound device captured by the processing device), an array of values that is the same size as the inputted image, where each pixel in the array consists of a probability that that pixel is where the tip of the ultrasound image is located in the inputted image. The processing device may then predict that the pixel having the highest probability represents the location of the tip of the ultrasound image and output the horizontal and vertical coordinates of this pixel.

In some embodiments, the statistical model may be trained to use regression to determine the horizontal and vertical components of the position of the ultrasound device relative to the processing device. Multiple images of the ultrasound device may be inputted to the statistical model as training input data. As training output data, each input image may be manually labeled with two numbers, namely the horizontal and vertical pixel coordinates of the tip of the ultrasound device in the image. Based on this training data, the statistical model may learn to output, based on an inputted image (e.g., a frame of the video of the ultrasound device captured by the processing device), the horizontal and vertical pixel coordinates of the tip of the ultrasound device in the image.

In some embodiments, the statistical model may be trained as a segmentation model to determine the horizontal and vertical components of the position of the ultrasound device relative to the processing device. Multiple images of the ultrasound device may be inputted to the statistical model as training input data. As training output data, a segmentation mask may be inputted to the statistical model, where the segmentation mask is an array of values equal in size to the image, and pixels corresponding to locations within the ultrasound device in the image are manually set to 1 and other pixels are set to 0. (While values of 1 and 0 are described, other values may be used instead.) Based on this training data, the statistical model may learn to output, based on an inputted image (e.g., a frame of the video of the ultrasound device captured by the processing device), a segmentation mask where each pixel has a value representing the probability that the pixel corresponds to a location within the ultrasound device in the image (values closer to 1) or outside the ultrasound device (values closer to 0). Horizontal and vertical pixel coordinates representing a single location of the ultrasound device in the image may then be derived (e.g., using averaging or some other method for deriving a single value from multiple values) from this segmentation mask.

In some embodiments, determining the position of ultrasound device along the depth dimension relative to the processing device may include determining the distance of a particular portion (e.g., the tip) of the ultrasound device from the processing device. In some embodiments, the processing device may use a statistical model (which may be the same as or different than any of the statistical models described herein) trained to determine the position of ultrasound device along the depth dimension relative to the processing device. In some embodiments, the statistical model may be trained to use regression to determine the position of ultrasound device along the depth dimension relative to the processing device. Multiple images of the ultrasound device may be inputted to the statistical model as training input data. As training output data, each input image may be manually labeled with one number, namely the distance of the tip of the ultrasound device from the processing device when the image was captured. In some embodiments, a depth camera may be used to generate the training output data. For example, the depth camera may use disparity maps or structure light cameras. Such cameras may be considered stereo cameras in that they may use two cameras at different locations on the processing device that simultaneously capture two images, and the disparity between the two images may be used to determine the depth of the tip of the ultrasound device depicted in both images. In some embodiments, the depth camera may be a time-of-flight camera may be used to determine the depth of the tip of the ultrasound device. In some embodiments, the depth camera may generate absolute depth values for the entire video frame, and because the position of the tip of the ultrasound probe in the video frame may be determined using the method described above, the distance of the tip of the ultrasound probe from the processing device may be determined. Based on this training data, the statistical model may learn to output, based on an inputted image (e.g., a frame of the video of the ultrasound device captured by the processing device), the distance of the tip of the ultrasound device from the processing device when the image was captured. In some embodiments, the processing device may use a depth camera to directly determine the depth of the tip of the ultrasound device, in the same manner discussed above for generating training data, without using a statistical model specifically trained to determine depth. In some embodiments, the processing device may assume a predefined depth as the depth of the tip of the ultrasound device relative to the processing device.

In some embodiments, using camera intrinsics (e.g., focal lengths, skew coefficient, and principal points), the processing device may convert the horizontal and vertical pixel coordinates of the tip of the ultrasound device into the horizontal (x-direction) and vertical (y-direction) distance of the tip of the ultrasound device relative to the processing device (more precisely, relative to the camera of the processing device). In some embodiments, the processing device may use the distance of the tip of the ultrasound device from the processing device (determined using any of the methods above) to convert the horizontal and vertical pixel coordinates of the tip of the ultrasound device into the horizontal (x-direction) and vertical (y-direction) distance of the tip of the ultrasound device relative to the processing device. It should be appreciated that while the above description has focused on using the tip of the ultrasound device to determine the position of the ultrasound device, any feature on the ultrasound device may be used instead.

In some embodiments, an auxiliary marker on the ultrasound device may be used to determine the distances of that feature relative to the processing device in the horizontal, vertical, and depth directions based on the video of the ultrasound device captured by the processing device, using pose estimation techniques and without using statistical models. For example, the auxiliary marker may be a marker conforming to the ArUco library, a color band, or some feature that is part of the ultrasound device itself.

The orientation of the ultrasound device relative to the processing device may include three degrees of freedom, namely the roll, pitch, and yaw angles relative to the processing device. In some embodiments, the processing device may use a statistical model (which may be the same as or different than any of the statistical models described herein) trained to determine the orientation of the ultrasound device relative to the processing device. In some embodiments, the statistical model may be trained to use regression to determine the orientation of the ultrasound device relative to the processing device. Multiple images of the ultrasound device may be inputted to the statistical model as training input data. As training output data, each input image may be manually labeled with three numbers, namely the roll, pitch, and yaw angles of the ultrasound device relative to the processing device when the image was captured. In some embodiments, the training output data may be generated using sensor data from the ultrasound device and sensor data from the processing device. The sensor data from the ultrasound device may be collected by a sensor on the ultrasound device (e.g., the sensor 106). The sensor data from the processing device may be collected by a sensor on the processing device (e.g., the sensor 118). The sensor data from each device may describe the acceleration of the device (e.g., as measured by an accelerometer), the angular velocity of the device (e.g., as measured by a gyroscope), and/or the magnetic field in the vicinity of the device (e.g., as measured by a magnetometer). Using sensor fusion techniques (e.g., based on Kalman filters, complimentary filters, and/or algorithms such as the Madgwick algorithm), this data may be used to generate the roll, pitch, and yaw angles of the device relative to a coordinate system defined by the directions of the local gravitational acceleration and the local magnetic field. If the roll, pitch, and yaw angles of each device are described by a rotation matrix, then multiplying the rotation matrix of the processing device by the inverse of the rotation matrix of the ultrasound device may produce a matrix describing the orientation (namely, the roll, pitch, and yaw angles) of the ultrasound device relative to the processing device. Based on this training data, the statistical model may learn to output, based on an inputted image (e.g., a frame of the video of the ultrasound device captured by the processing device), the orientation of the ultrasound device relative to the processing device when the image was captured. This method will be referred to below as the "statistical model method."

In some embodiments, the processing device may use, at any given time, the sensor data from the ultrasound device and the sensor data from the processing to directly determine orientation at that particular time, without using a statistical model. In other words, at a given time, the processing device may use the sensor data collected by the ultrasound device at that time and the sensor data collected by the processing device at that time to determine the orientation of the ultrasound device relative to the processing device at that time (e.g., using sensor fusion techniques as described above). This method will be referred to below as the "sensor method."

In some embodiments, if the processing device performs the sensor method using data from accelerometers and gyroscopes, but not magnetometers, on the ultrasound device and the processing device, the processing device may accurately determine orientations of the ultrasound device and the processing device except for the angle of the devices around the direction of gravity. It may be helpful not to use magnetometers, as this may obviate the need for sensor calibration, and because external magnetic fields may interfere with measurements of magnetometers on the ultrasound and processing devices. In some embodiments, if the processing device performs the statistical model method, the processing device may accurately determine the orientation of the ultrasound device relative to the processing device, except that the statistical model method may not accurately detect when the ultrasound device rotates around its long axis as seen from the reference frame of the processing device. This may be due to symmetry of the ultrasound device about its long axis. In some embodiments, the processing device may perform both the statistical model method and the sensor method, and combine the determinations from both methods to compensate for weaknesses of either method. For example, as described above, using the sensor method, the processing device may not accurately determine orientations of the ultrasound device and the processing device around the direction of gravity when not using magnetometers. Since, ultimately, determining the orientation of the ultrasound device relative to the processing device may be desired, it may only be necessary to determine the orientation of the ultrasound device around the direction of gravity as seen from the reference frame of the processing device. Thus, in some embodiments, the processing device may use the sensor method (using just accelerometers and gyroscopes) for determining orientation of the ultrasound device relative to the processing device except for determining the orientation of the ultrasound device around the direction of gravity as seen from the reference frame of the processing device, which the processing device may use the statistical model to determine. In such embodiments, rather than using a statistical model trained to determine the full orientation of the ultrasound device relative to the processing device, the statistical model may be specifically trained to determine, based on an inputted image, the orientation of the ultrasound device around the direction of gravity as seen from the reference frame of the processing device. In general, the processing device may combine determinations from the statistical model method and the sensor method to produce a more accurate determination.

In some embodiments, a statistical model may be trained to locate three different features of the ultrasound device in the video of the ultrasound device captured by the processing device (e.g., using methods described above for locating a portion of an ultrasound device, such as the tip, in an image), from which the orientation of the ultrasound device may be uniquely determined.

In some embodiments, the training output data for both position and orientation may be generated by manually labeling, in images of ultrasound devices captured by processing devices (the training input data), key points on the ultrasound device, and then an algorithm such as Solve PnP may determine, based on the key points, the position and orientation of the ultrasound device relative to the processing device. A statistical model may be trained on this training data to output, based on an inputted image of an ultrasound device captured by a processing device, the position and orientation of the ultrasound device relative to the processing device.

It should be appreciated that determining a position and/or orientation of the ultrasound device relative to the processing device may include determining any component of position and any component of orientation. For example, it may include determining only one or two of the horizontal, vertical, and depth dimensions of position and/or only one or two of the roll, pitch, and yaw angles. The process 200 proceeds from act 202 to act 204.

In act 204, the processing device displays, on a display screen of the processing device, an instruction for moving the ultrasound device. The instruction may be an instruction for moving the ultrasound device from its current position and orientation relative to a subject being imaged to a target position and orientation at which the ultrasound device may collect, from the subject, an ultrasound image depicting a target anatomical view (e.g., a parasternal long-axis view of the heart). The instruction may include a directional indicator (e.g., an arrow) superimposed on the video, where the directional indicator indicates the instruction for moving the ultrasound device. For example, if the instruction is to move the ultrasound device in the superior direction relative to the subject, the processing device may display an arrow pointing in the superior direction relative to the subject as depicted in the video. The instruction superimposed on the video may be considered an augmented-reality (AR) interface. The instruction may be generated based on the ultrasound data collected by the ultrasound device. In some embodiments, the processing device may generate the instruction for moving the ultrasound device. In some embodiments, the ultrasound device may generate the instruction and transmit the instruction to the processing device for display. In some embodiments, the processing device may transmit the ultrasound image to a remote server which may generate the instruction and transmit the instruction to the processing device for display. Further description of generating instructions for moving the ultrasound device 106 may be found in U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application) and published as U.S. Pat. Pub. 2017/0360401 A1. In some embodiments, rather than an instruction being generated, a remote expert may provide the instruction. For example, the processing device may transmit the video captured in act 202 and/or ultrasound data collected by the ultrasound device to a remote expert's processing device. The remote expert may determine, based on the video and/or the ultrasound data, how the ultrasound device must be moved and transmit, from his/her processing device, an instruction to the processing device for moving the ultrasound device. The processing device may then display the instruction simultaneously with the video on the display screen.

The processing device displays the instruction on the display screen based on the position and/or orientation of the ultrasound device relative to the processing device (as determined in act 202). In some embodiments, the processing device may determine an arrow to display as an instruction, translate and/or rotate that arrow in three-dimensional space based on the position and/or orientation of the ultrasound device relative to the processing device, and then project that three-dimensional arrow into two-dimensional space for display on the display screen of the processing device. The processing device may thus determine, based on the position and/or orientation of the ultrasound device relative to the processing device, the positioning of the arrow on the display screen and how the arrow appears to be rotated in three dimensions.

In some embodiments, the subject being imaged may be oriented in a default orientation relative to gravity. For example, the subject being imaged may be lying on his/her left side, such that moving the ultrasound device towards the subject's left side is in the direction of gravity, moving the ultrasound device towards the subject's head is 90 degrees relative to gravity, moving the ultrasound device toward the subject's right side is 180 degrees relative to gravity, and moving the ultrasound device towards the subject's legs is 270 degrees relative to gravity. Alternatively, the subject may be sitting. The processing device may receive a selection of whether the subject is lying on his/her left side or sitting. The processing device may receive an instruction to move the ultrasound device in a particular direction relative to the subject, calculate the orientation of the ultrasound device relative to the subject, and display an arrow relative to the ultrasound device by adjusting the display of the arrow based on the orientation of the ultrasound device relative to the subject. The processing device may instruct the user how to initially orient the ultrasound device in a known orientation around the direction of gravity, and then if the orientation of the subject relative to gravity is known, the orientation of the ultrasound device relative to the subject may be known. Thus, the processing device may be able to display arrows in a particular direction relative to the subject based on the orientation of the ultrasound device around the direction of gravity. Then, the processing device may track any deviation of the ultrasound device from the initial orientation relative to the subject (by tracking any deviation around the direction of gravity). The processing device may use this tracked deviation to compensate for the deviation and ensure that it continues to display the arrow in the desired direction relative to the subject.

Various inventive concepts may be embodied as one or more processes, of which an example has been provided. The acts performed as part of the process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps. For example, in some embodiments, act 204 may be absent, and the position and/or orientation of the ultrasound device relative to the processing device may be used for another purpose besides instructing a user how to move the ultrasound device.

Figure 4:
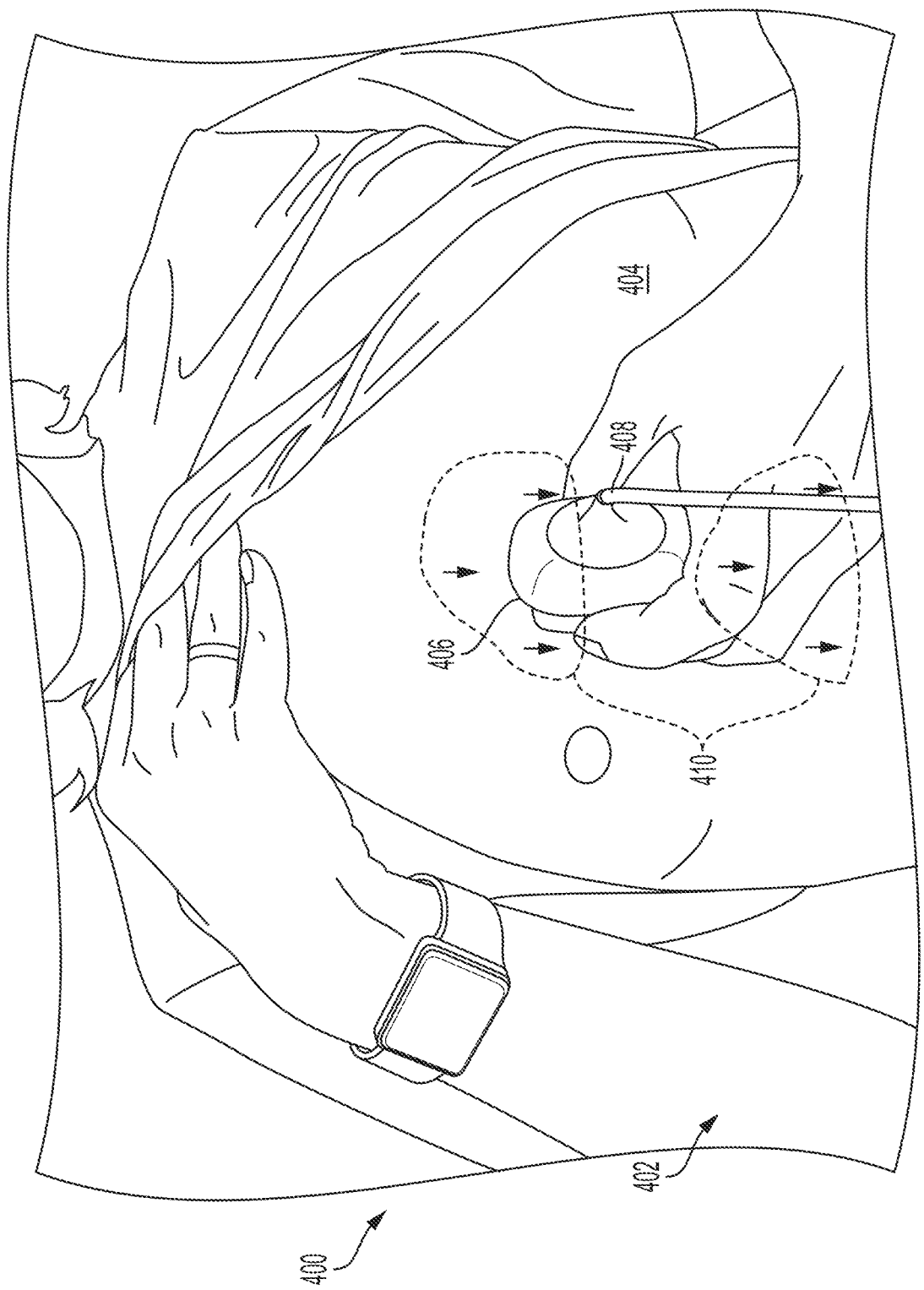
FIG. 4 illustrates an example augmented reality (AR) interface depicting an instruction for moving an ultrasound device, in accordance with certain embodiments described herein.

FIG. 4 illustrates an example augmented reality (AR) interface 400 depicting an instruction for moving an ultrasound device, in accordance with certain embodiments described herein. The AR interface 400 includes a video 402, a subject 404, an ultrasound device 406, and an instruction 410. The ultrasound device 406 has a tip 408. The video 402 may be captured by a camera on a processing device that displays the AR interface 400. The instruction 410 includes a plurality of arrows pointing in a particular direction, indicating that the ultrasound device 406 should be translated in that particular direction.

Figure 5:
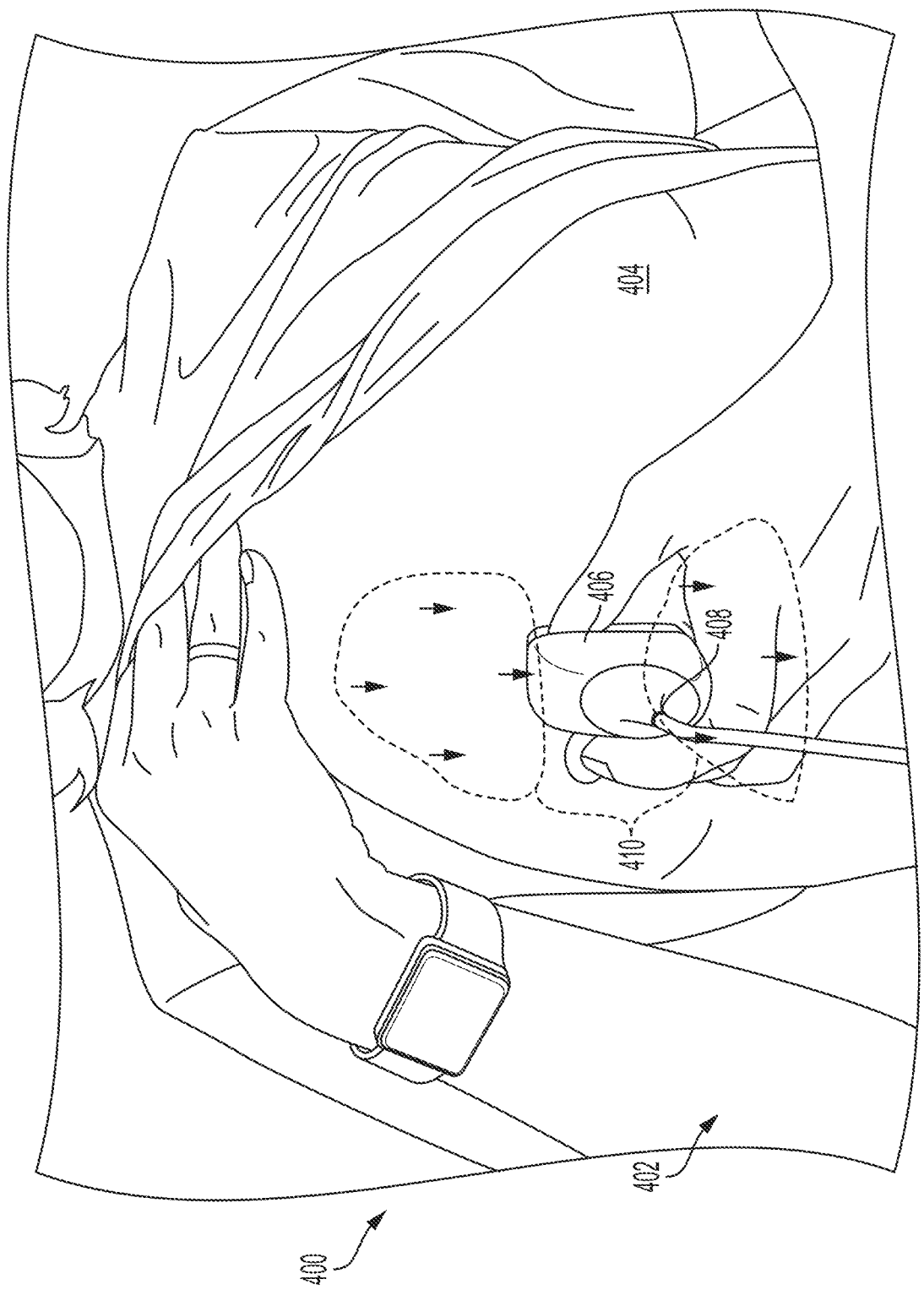
FIG. 5 illustrates another example of the AR interface of FIG. 4, in accordance with certain embodiments described herein.

FIG. 5 illustrates another example of the AR interface 400, in accordance with certain embodiments described herein. In FIG. 5, the ultrasound device 406, and in particular the tip 408 of the ultrasound device 406, has changed location from the location in FIG. 4. The instruction 410 has also changed position from the location in FIG. 4. As described above, the processing device may determine the instruction 410 to be displayed, translate and/or rotate that instruction 410 in three-dimensional space based on the position and/or orientation of the ultrasound device 406 relative to the processing device, and then project that three-dimensional instruction 410 into two-dimensional space for display on the AR interface 400. In FIGS. 4-5, there is a significant difference in position of the tip 408 of the ultrasound device 406 but not a significant difference in orientation of the ultrasound device relative to the processing device, and thus the change in position of the instruction 410 (rather than a change in rotation of the instruction 410) is most significant.

Figure 6:
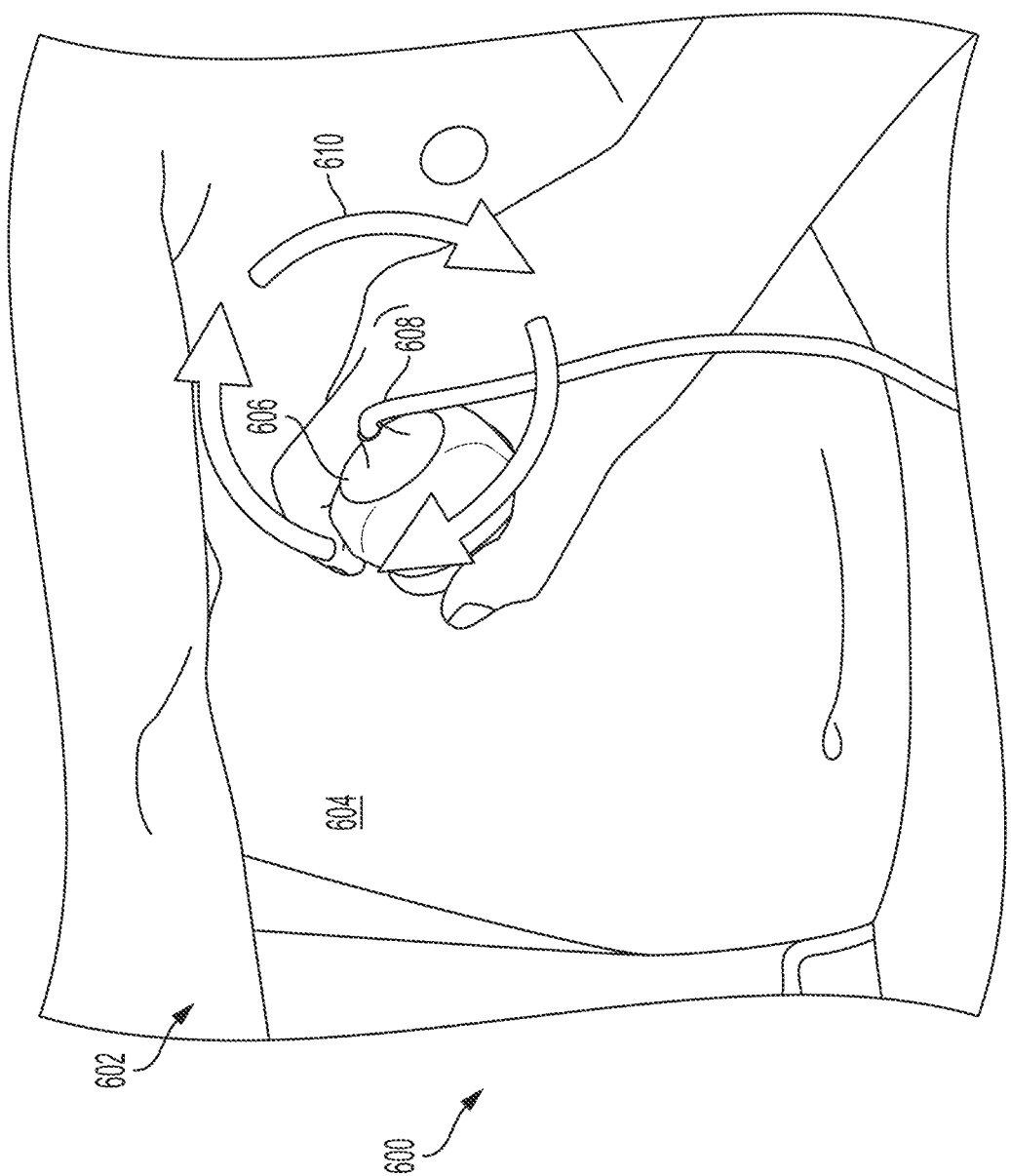
FIG. 6 illustrates an example AR interface depicting an instruction for moving an ultrasound device, in accordance with certain embodiments described herein.

FIG. 6 illustrates an example AR interface 600 depicting an instruction for moving an ultrasound device, in accordance with certain embodiments described herein. The AR interface 600 includes a video 602, a subject 604, an ultrasound device 606, and an instruction 610. The ultrasound device 606 has a tip 608. The video 602 may be captured by a camera on a processing device that displays the AR interface 600. The instruction 610 includes a plurality of arrows indicating that the ultrasound device 606 should be rotated clockwise.

Figure 7:
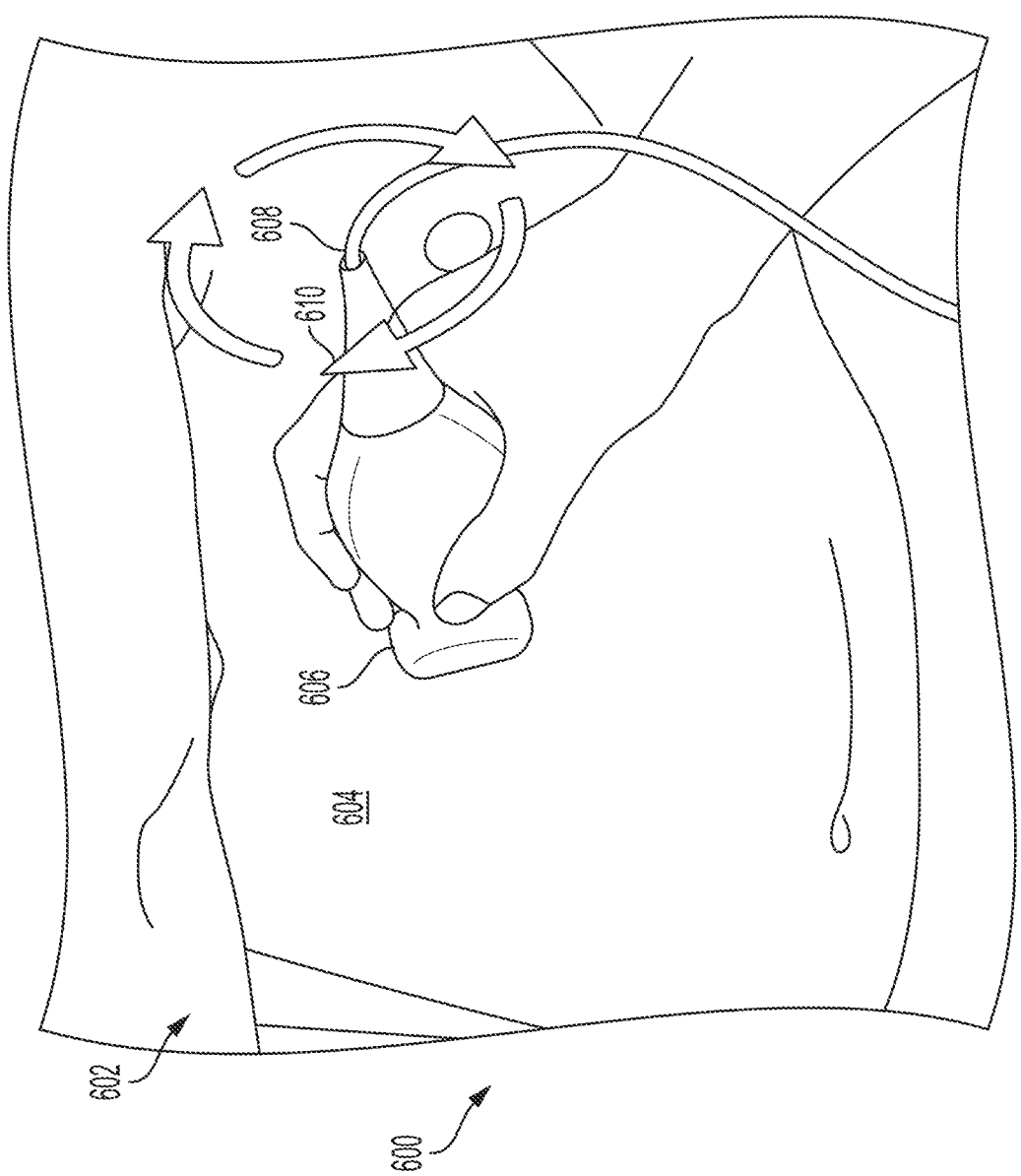
FIG. 7 illustrates another example of the AR interface of FIG. 6, in accordance with certain embodiments described herein.

FIG. 7 illustrates another example of the AR interface 600, in accordance with certain embodiments described herein. In FIG. 7, the tip 608 of the ultrasound device 606 has changed position from the position in FIG. 6, and the ultrasound device 606 has changed orientation from the orientation in FIG. 6. The position and orientation of the instruction 610 has therefore also changed. As described above, the processing device may determine the instruction 610 to be displayed, translate and/or rotate that instruction 610 in three-dimensional space based on the position and/or orientation of the ultrasound device 606 relative to the processing device, and then project that three-dimensional instruction 610 into two-dimensional space for display on the AR interface 600. In FIGS. 6-7, there is a significant difference in horizontal position and vertical position of the tip 608 of the ultrasound device 606 relative to the processing device, and thus there is a significant change in horizontal position and vertical position of the instruction 610. There is also a significant difference in orientation of the ultrasound device 606 relative to the processing device, and thus a significant difference in and how the instruction 610 appears to be rotated in three dimensions.

Aspects of the technology described herein relate to the application of automated image processing techniques to analyze images, such as ultrasound images. In some embodiments, the automated image processing techniques may include machine learning techniques such as deep learning techniques. Machine learning techniques may include techniques that seek to identify patterns in a set of data points and use the identified patterns to make predictions for new data points. These machine learning techniques may involve training (and/or building) a model using a training data set to make such predictions.

Deep learning techniques may include those machine learning techniques that employ neural networks to make predictions. Neural networks typically include a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input, for example, to weight some inputs higher than others. Example transfer functions that may be employed include step functions, piecewise linear functions, and sigmoid functions. These neurons may be organized into a plurality of sequential layers that each include one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may include a set of example inputs and an answer associated with each input. For example, the training data may include a plurality of images of ultrasound devices labeled with the horizontal and vertical pixel coordinates of the tip of the ultrasound device. In this example, the images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

Once the training data has been created, the training data may be loaded to a database (e.g., an image database) and used to train a neural network using deep learning techniques. Once the neural network has been trained, the trained neural network may be deployed to one or more processing devices.

Figure 8:
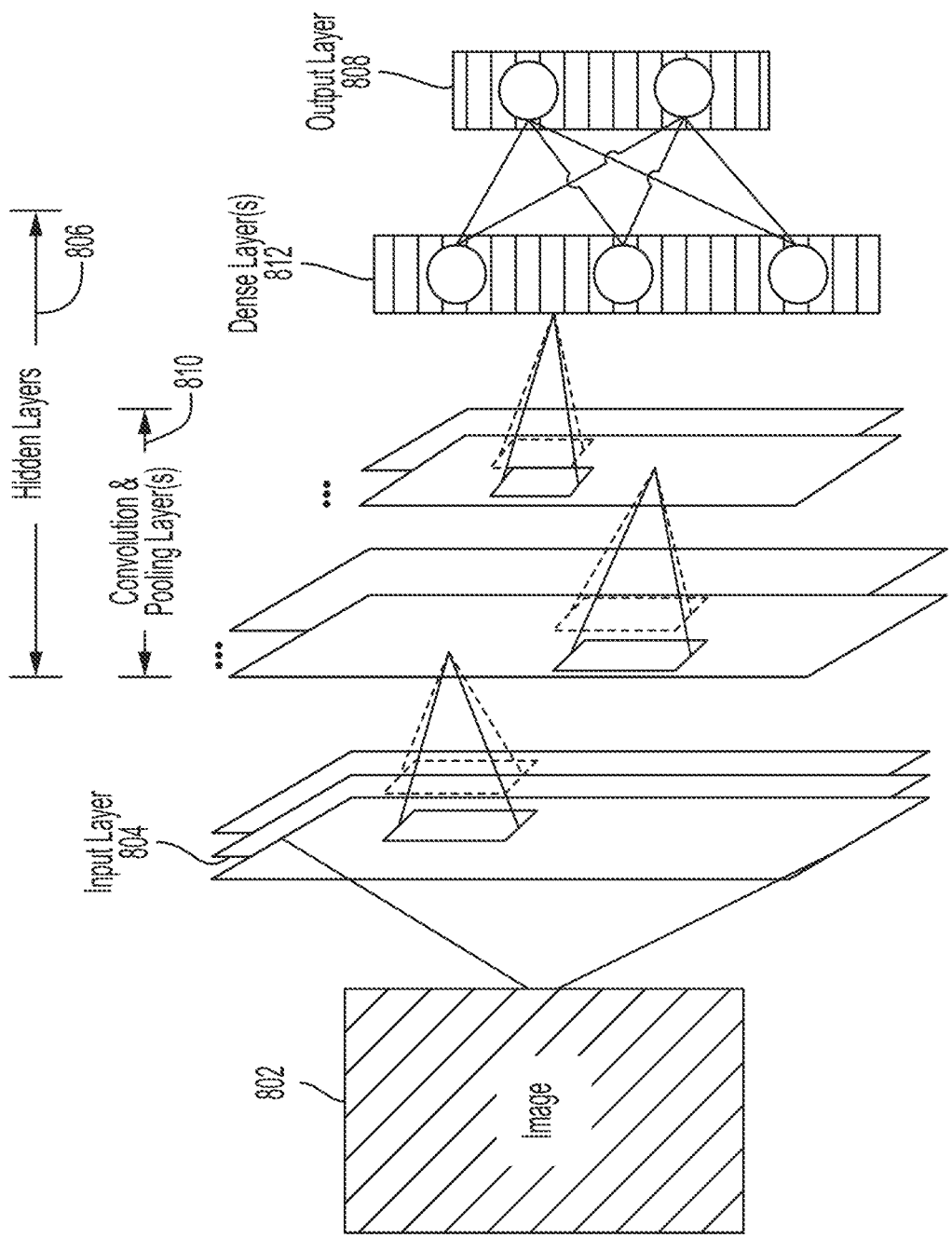
FIG. 8 illustrates an example convolutional neural network that is configured to analyze an image, in accordance with certain embodiments described herein.

In some applications, a neural network may be implemented using one or more convolution layers to form a convolutional neural network. An example convolutional neural network that is configured to analyze an image 802 is shown in FIG. 8, in accordance with certain embodiments described herein. As shown, the convolutional neural network includes an input layer 804 to receive the image 802, an output layer 808 to provide the output, and a plurality of hidden layers 806 connected between the input layer 804 and the output layer 808. The plurality of hidden layers 806 includes convolution and pooling layers 810 and dense layers 812.

The input layer 804 may receive the input to the convolutional neural network. As shown in FIG. 8, the input the convolutional neural network may be the image 802. The image 802 may be, for example, an image of an ultrasound device.

The input layer 804 may be followed by one or more convolution and pooling layers 810. A convolutional layer may include a set of filters that are spatially smaller (e.g., have a smaller width and/or height) than the input to the convolutional layer (e.g., the image 802). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 810 may be followed by dense layers 812. The dense layers 812 may include one or more layers each with one or more neurons that receives an input from a previous layer (e.g., a convolutional or pooling layer) and provides an output to a subsequent layer (e.g., the output layer 808). The dense layers 812 may be described as "dense" because each of the neurons in a given layer may receive an input from each neuron in a previous layer and provide an output to each neuron in a subsequent layer. The dense layers 812 may be followed by an output layer 808 that provides the outputs of the convolutional neural network. The outputs may be, for example, the horizontal and vertical pixel coordinates of the tip of the ultrasound device in the image 802.

It should be appreciated that the convolutional neural network shown in FIG. 8 is only one example implementation and that other implementations may be employed. For example, one or more layers may be added to or removed from the convolutional neural network shown in FIG. 8. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

For further description of deep learning techniques, see U.S. patent application Ser. No. 15/626,423 titled "AUTOMATIC IMAGE ACQUISITION FOR ASSISTING A USER TO OPERATE AN ULTRASOUND DEVICE," filed on Jun. 19, 2017 (and assigned to the assignee of the instant application). It should be appreciated that statistical models described herein may be, for example, a convolutional neural network, a fully connected neural network, a recurrent neural network (e.g., a long short-term memory (LSTM) recurrent neural network), a random forest, a support vector machine, a linear classifier, and/or any other statistical model.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. A method of operating an ultrasound system, the method comprising:
   determining, by a processing device in operative communication with an ultrasound device, a horizontal position, a vertical position, and a depth of the ultrasound device relative to the processing device using one or more first statistical models and a video collected by a camera of the processing device which depicts the ultrasound device;
   determining, using a sensor on the ultrasound device, a sensor on the processing device, one or more second statistical models, and the video collected by the camera of the processing device which depicts the ultrasound device, an orientation of the ultrasound device relative to the processing device; and
   displaying on a display screen of the processing device, based on at least one selected from a group consisting of:
      the horizontal position,
      the vertical position,
      the depth, and
      the orientation of the ultrasound device relative to the processing device, an instruction for moving the ultrasound device.

2. The method of claim 1, wherein determining the orientation of the ultrasound device using the sensor on the ultrasound device and the sensor on the processing device comprises using an accelerometer and gyroscope on the ultrasound device and an accelerometer and gyroscope on the processing device.

3. The method of claim 1, wherein determining the orientation of the ultrasound device comprises:
determining, using the sensor on the ultrasound device and the sensor on the processing device, an orientation of the ultrasound device relative to the processing device except for determining an orientation of the ultrasound device around a direction gravity as seen from a reference frame of the processing device; and
determining, using the one or more second statistical models and the video collected by the camera of the processing device which depicts the ultrasound device, the orientation of the ultrasound device around the direction gravity as seen from the reference frame of the processing device.

4. The method of claim 1, wherein determining the horizontal position and the vertical position of the ultrasound device relative to the processing device comprises locating a tip of the ultrasound device in the video collected by the processing device which depicts the ultrasound device.

5. The method of claim 1, further comprising receiving, by the processing device, a selection of whether a subject being imaged is lying on his/her left side or sitting.

6. The method of claim 1, wherein a subject being imaged is oriented in a default orientation relative to a direction of gravity.

7. The method of claim 1, further comprising instructing, by the processing device, a user how to orient the ultrasound device in an initial orientation around a direction of gravity.

8. The method of claim 7, further comprising:
tracking, by the processing device, a deviation of the ultrasound device from an initial orientation relative to a subject being imaged by tracking a deviation of the ultrasound device from the initial orientation around the direction of gravity; and
displaying a direction indicator corresponding to the instruction for moving the ultrasound device by compensating for the deviation such that the directional indicator is in the desired direction relative to the subject being imaged.

9. The method of claim 1, wherein displaying the instruction for moving the ultrasound device comprises:
at least one selected from a group consisting of translating and rotating a directional indicator corresponding to the instruction in three-dimensional space based on at least one selected from a group consisting of:
the horizontal position,
the vertical position,
the depth, and
the orientation of the ultrasound device relative to the processing device; and
projecting that three-dimensional arrow into two-dimensional space for display on the display screen of the processing device.

10. A non-transitory computer readable medium comprising processor-executable instructions which, when executed, cause a processor on a processing device in operative communication with an ultrasound device to:
determine a horizontal position, a vertical position, and a depth of the ultrasound device relative to the processing device using one or more first statistical models and a video collected by a camera of the processing device which depicts the ultrasound device;
determine, using sensor data from a sensor on the ultrasound device, sensor data from a sensor on the processing device, one or more second statistical models, and the video collected by the camera of the processing device which depicts the ultrasound device, an orientation of the ultrasound device relative to the processing device; and
display on a display screen of the processing device, based on at least one selected from a group consisting of:
the horizontal position,
the vertical position,
the depth, and
the orientation of the ultrasound device relative to the processing device, an instruction for moving the ultrasound device.

11. The non-transitory computer readable medium of claim 10, wherein the instructions which cause the processor to determine the orientation of the ultrasound device relative to the processing device using sensor data from a sensor on the ultrasound device, sensor data from a sensor on the processing device, one or more second statistical models, and the video collected by the camera of the processing device which depicts the ultrasound device, comprise instructions which, when executed, cause the processor to determine the orientation of the ultrasound device using data from an accelerometer and gyroscope on the ultrasound device and data from an accelerometer and gyroscope on the processing device.

12. The non-transitory computer readable medium of claim 10, wherein the instructions which cause the processor to determine the orientation of the ultrasound device relative to the processing device using sensor data from a sensor on the ultrasound device, sensor data from a sensor on the processing device, one or more second statistical models, and the video collected by the camera of the processing device which depicts the ultrasound device, comprise instructions which, when executed, cause the processor to determine the orientation of the ultrasound device relative to the processing device by:
determining, using the sensor on the ultrasound device and the sensor on the processing device, an orientation of the ultrasound device relative to the processing device except for determining an orientation of the ultrasound device around a direction gravity as seen from a reference frame of the processing device; and
determining, using the one or more second statistical models and the video collected by the camera of the processing device which depicts the ultrasound device, the orientation of the ultrasound device around the direction gravity as seen from the reference frame of the processing device.

13. The non-transitory computer readable medium of claim 10, wherein the instructions which cause the processor to determine the horizontal position and the vertical position of the ultrasound device relative to the processing device comprise instructions which, when executed, cause the processor to locate a tip of the ultrasound device in the video collected by the processing device which depicts the ultrasound device.

14. The non-transitory computer readable medium of claim 10, wherein the instructions, when executed, further cause the processor to receive a selection of whether a subject being imaged is lying on his/her leftside or sitting.

15. The non-transitory computer readable medium of claim 10, wherein the instructions, when executed, further cause the processor to determine whether a subject being imaged is oriented in a default orientation relative to a direction of gravity.

16. The non-transitory computer readable medium of claim 10, wherein the instructions, when executed, further cause the processor to instruct a user how to orient the ultrasound device in an initial orientation around a direction of gravity.

* * * * *